(12) United States Patent
Martin, II et al.

(10) Patent No.: US 12,213,796 B2
(45) Date of Patent: Feb. 4, 2025

(54) AROMA TRAINING USING VIRTUAL REALITY

(71) Applicant: Accenture Global Solutions Limited, Dublin (IE)

(72) Inventors: Derrick Anthony Martin, II, Brooklyn, NY (US); Alex M. Kass, Palo Alto, CA (US); Marc Carrel-Billiard, Vence (FR); Alexandria Emily Pabst, Merced, CA (US)

(73) Assignee: Accenture Global Solutions Limited, Dublin (IE)

( * ) Notice: Subject to any disclaimer, the term of this patent is extended or adjusted under 35 U.S.C. 154(b) by 9 days.

(21) Appl. No.: 17/843,442

(22) Filed: Jun. 17, 2022

(65) Prior Publication Data
US 2023/0172524 A1 Jun. 8, 2023

Related U.S. Application Data

(60) Provisional application No. 63/286,744, filed on Dec. 7, 2021.

(51) Int. Cl.
*A61B 5/00* (2006.01)
*G06F 3/01* (2006.01)
*G06F 3/04842* (2022.01)

(52) U.S. Cl.
CPC ............ *A61B 5/4011* (2013.01); *G06F 3/015* (2013.01); *G06F 3/04842* (2013.01)

(58) Field of Classification Search
CPC .... A61B 5/4011; G06F 3/015; G06F 3/04842
See application file for complete search history.

(56) References Cited

U.S. PATENT DOCUMENTS 8,321,797 B2 * 11/2012 Perkins ................. G06Q 30/02
715/757
9,717,454 B2 * 8/2017 Mills .................... A61B 5/4088
(Continued)

FOREIGN PATENT DOCUMENTS

CN 107015660 A * 8/2017 ............. A61B 5/381
KR 10-2020-0107395 9/2020
(Continued)

OTHER PUBLICATIONS

Bioinspired Smell and Taste Sensors, 1st ed., Wang et al. (eds.), 2015, 330 pages.
(Continued)

*Primary Examiner* — Xuan M Thai
*Assistant Examiner* — Sadaruz Zaman
(74) *Attorney, Agent, or Firm* — Polsinelli PC

(57) ABSTRACT

Methods, systems, and apparatus, including computer programs encoded on a computer storage medium, for implementing an olfaction training program by an online service executing on a server. A first object and an aroma of the first object is transmitted to the client device of a user that presents the first object in a virtual reality environment and disperses the first aroma. In response, the user interacts with the vital reality environment. The user response is transmitted back to the online service. The user response is stored in a database along with the first data and the first aroma. The online service determines a second object and an aroma of the second object based on the user response. The second object and the aroma of the second object is transmitted to the client device.

16 Claims, 5 Drawing Sheets

(56) References Cited

U.S. PATENT DOCUMENTS

| | | | | |
|---|---|---|---|---|
| 9,907,876 | B2* | 3/2018 | Jin | A61L 9/122 |
| 9,925,458 | B2* | 3/2018 | Fateh | A63F 13/28 |
| 10,437,266 | B2* | 10/2019 | Hasenoehrl | A61L 9/14 |
| 10,688,389 | B2* | 6/2020 | Flego | A63F 13/52 |
| 11,216,068 | B2* | 1/2022 | Dong | G06F 3/015 |
| 11,351,450 | B2* | 6/2022 | Flego | G06F 3/016 |
| 2010/0163027 | A1* | 7/2010 | Hyde | G16H 20/13 |
| | | | | 128/203.12 |
| 2010/0168525 | A1* | 7/2010 | Hyde | A61B 5/163 |
| | | | | 600/300 |
| 2010/0233662 | A1* | 9/2010 | Casper | G09B 19/04 |
| | | | | 434/185 |
| 2014/0282105 | A1* | 9/2014 | Nordstrom | G06F 3/016 |
| | | | | 715/753 |
| 2014/0377130 | A1* | 12/2014 | Edwards | G05B 15/02 |
| | | | | 422/5 |
| 2018/0050171 | A1* | 2/2018 | Tabert | C11D 3/50 |
| 2018/0280556 | A1* | 10/2018 | Fateh | B05B 7/1613 |
| 2019/0142326 | A1* | 5/2019 | Mills | A61B 5/4011 |
| | | | | 600/303 |
| 2021/0106910 | A1* | 4/2021 | Jain | G05B 15/02 |
| 2022/0203225 | A1* | 6/2022 | Jain | G06F 3/013 |
| 2023/0172524 | A1* | 6/2023 | Martin, II | A61B 5/4011 |

FOREIGN PATENT DOCUMENTS

| | | | | |
|---|---|---|---|---|
| WO | WO-2016164917 | A1 * | 10/2016 | A61L 9/035 |
| WO | WO-2019164737 | A1 * | 8/2019 | A63F 13/25 |

OTHER PUBLICATIONS

ClevelandClinic.org [online], "Treating Smell Loss in COVID-19 Patients," Mar. 17, 2021, retrieved on Dec. 9, 2022, retrieved from URL<https://consultqd.clevelandclinic.org/treating-smell-loss-in-covid-19-patients/>, 5 pages.

ClinicalTrials.gov [online], "Visual-OLfactory Training in Participants With COVID-19 Resultant Loss of Smell (VOLT)," NCT04710394, last updated Jun. 21, 2022, retrieved on Dec. 9, 2022, retrieved from URL<https://clinicaltrials.gov/ct2/show/study/NCT04710394>, 32 pages.

Ezzatdoost et al., "Decoding olfactory stimuli in EEG data using nonlinear features: A pilot study," Journal of Neuroscience Methods, May 16, 2020, 341:108780, 10 pages.

Gellrich et al., "Brain volume changes in hyposmic patients before and after olfactory training," The Laryngoscope, Dec. 14, 2017, 128(7):1531-1536.

Guducu et al., "Separating Normosmic and Anosmic Patients Based on Entropy Evaluation of Olfactory Event-Related Potentials," Brain Research, Dec. 8, 2018, 1708:78-83.

Harvard.edu [online], "How COVID-19 Causes Loss of Smell," Jul. 24, 2020, retrieved on Dec. 9, 2022, retrieved from URL<https://hms.harvard.edu/news/how-covid-19-causes-loss-smell>, 9 pages.

Henkin et al., "Improvement in smell and taste dysfunction after repetitive transcranial magnetic stimulation," American Journal of Otolaryngology, Jan./Feb. 2011, 32(1):38-46.

Iravani et al., "Non-invasive recording from the human olfactory bulb," Nature Communications, Jan. 31, 2020, 11(1):648, 10 pages.

Jacquot et al., "Influence of nasal trigeminal stimuli on olfactory sensitivity," Comptes Rendus Biologies, Apr. 2004, 327(4):305-311.

Klemm et al., "Topographical EEG maps of human responses to odors," Chemical Senses, 1992, 17(3):347-361.

Kollndorfer et al., "Olfactory training induces changes in regional functional connectivity in patients with long-term smell loss," NeuroImage: Clinical, 2015, 9:401-410.

Lorig et al., "EEG activity during administration of low-concentration odors," Bulletin of the Psychonomic Society, 1990, 28(5):405-408.

Lorig et al., "Visual event-related potentials during odor labeling," Chemical Senses, 1993, 18(4):379-387.

Masaoka et al., "The neural cascade of olfactory processing: A combined fMRI-EEG study," Respiratory Physiology & Neurobiology, Dec. 1, 2014, 204:71-77.

NYTimes.com [online], "Virtual Reality Therapy Plunges Patients Back Into Trauma. Here Is Why Some Swear by It," Jun. 3, 2021, retrieved on Dec. 9, 2022, retrieved from URL<https://www.nytimes.com/2021/06/03/well/mind/vr-therapy.html>, 6 pages.

Olofsson et al., "Smell-Based Memory Training: Evidence of Olfactory Learning and Transfer to the Visual Domain," Chemical Senses, Jul. 9, 2020, 45(7):593-600.

Parastarfeizabadi et al., "Advances in closed-loop deep brain stimulation devices," Journal of NeuroEngineering and Rehabilitation, Aug. 11, 2017, 14(1):79, 20 pages.

Pellegrino et al., "Bimodal odor processing with a trigeminal component at sub- and suprathreshold levels," Neuroscience, Nov. 5, 2017, 363:43-49.

RoadToVR.com [online], "Feelreal VR Scent Mask Hits Roadblock Amidst Crackdown on Flavored Vaping Products," Jan. 2, 2020, retrieved on Dec. 9, 2022, retrieved from URL<https://www.roadtovr.com/feelreal-vr-scent-mask-vaping-fda-ban/>, 4 pages.

SensoryCots.com [online], "Fire Training and Learning," available on or before Aug. 4, 2020 via Internet Archive: Wayback Machine URL<https://web.archive.org/web/20200804224954/https://sensorycots.com/fire-training-and-learning>, retrieved on Dec. 9, 2022, retrieved from URL<https://sensorycots.com/fire-training-and-learning>, 3 pages.

TechMoneyFit.com [online], "FeelReal VR Scent Mask Banned Temporarily by FDA, Considered Vaping Product," Jan. 5, 2020, retrieved on Dec. 9, 2022, retrieved from URL<https://web.archive.org/web/20200921201533/https://techmoneyfit.com/blog/feelreal-vr-scent-mask-banned-temporarily-by-fda-considered-vaping-product/>, 4 pages.

TheConversation.com [online], "COVID killed your sense of smell? Here's how experts train people to get theirs back," Jan. 26, 2021, retrieved on Dec. 9, 2022, retrieved from URL<https://theconversation.com/covid-killed-your-sense-of-smell-heres-how-experts-train-people-to-get-theirs-back-150989>, 3 pages.

Trachtenberg et al., "Long-term in vivo imaging of experience-dependent synaptic plasticity in adult cortex," Nature, Dec. 19, 2002, 420(6917):788-794.

Viczko et al., "Effects on Mood and EEG States After Meditation in Augmented Reality With and Without Adjunctive Neurofeedback," Frontiers in Virtual Reality, Mar. 22, 2021, 2:618381, 15 pages.

VRGear.com [online], "Feelreal VR Scent Mask on Temporary Ban, Considered 'Flavored Vaping Product'," Jan. 2, 2020, retrieved on Dec. 9, 2022, retrieved from URL<https://vrgear.com/news/feelreal-vr-scent-mask-on-temporary-ban-considered-flavored-vaping-product/>, 3 pages.

WUSTL.edu [online], "COVID-19, losing one's sense of smell and regaining it," Dec. 1, 2020, retrieved on Dec. 9, 2022, retrieved from URL<https://oto.wustl.edu/covid-19-losing-one-sense-of-smell-and-regaining-it/>, 3 pages.

Amores et al., "Promoting Relaxation Using Virtual Reality, Olfactory Interfaces and Wearable EEG," Presented at Proceedings of the 2018 IEEE 15th International Conference on Wearable and Implantable Body Sensor Networks (BSN), Las Vegas, NV, USA, Mar. 4-7, 2018, 98-101.

Extended Search Report in European Appln. No. 22208538.3, dated Apr. 19, 2023, 11 pages.

Jung et al., "The Impact of Multi-sensory Stimuli on Confidence Levels for Perceptual-cognitive Tasks in VR," Presented at Proceedings of the 2020 IEEE Conference on Virtual Reality and 3D User Interfaces (VR), Atlanta, GA, USA, Mar. 22-26, 2020, 463-472.

Tiele et al., "Wine Aroma Sensory Training Game Employing a Thermal Based Olfactory Display," Presented at Proceedings of the 2019 IEEE International Symposium on Olfaction and Electronic Nose (ISOEN), Fukuoka, Japan, May 26-29, 2019, 3 pages.

\* cited by examiner

AROMA TRAINING USING VIRTUAL REALITY

CROSS-REFERENCE TO RELATED APPLICATION

This application claims the benefit of U.S. Provisional Application No. 63/286,744, filed Dec. 7, 2021, and titled "Aroma Synthesis for Olfactory Training," which is incorporated by reference.

TECHNICAL FIELD

This specification relates to olfactory based multisensory virtual reality, to generate a sequence of stimuli for users based on user activity.

BACKGROUND

Olfaction is one of the five primary human senses that allows humans to experience the physical world. It plays an important role in detecting hazards such as fire or toxic fumes while also allowing humans to enjoy food. Olfaction deficiency (OD) can therefore be associated to a plurality of health issues such as depression, decreased nutrition which can have a negative impact on the quality of life. Due to the COVID-19 pandemic, there is an increase in the number of people suffering from post-viral olfactory dysfunction (PVOD) resulting in a large number of people to have OD with no promising cure.

Virtual reality (VR) refers to a computer-generated three dimensional (3D) environment that a user can experience. The user can interact with the virtual environment via electronic hardware such as a VR headset with a display screen, gloves or other clothing/accessories that are fitted with sensors (such as motion sensors), actuators, etc. Recent advances in technology has led VR technology to expand beyond the audio-visual and virtual motion setting by incorporating the sense of aroma (olfaction). This is generally achieved by adding a device such as an atomizer that can include a dispersing agent and an electronically controlled valve to a VR headset that can be used to release dispersing agent to generate aroma conditions in a 3D virtual environment.

SUMMARY

This specification generally describes a techniques and methods of generating OD treatment plan in a VR environment using a VR headset capable of dispersing aroma. The techniques and methods are implemented in a distributed environment where users undertake an OD treatment using VR headsets. The techniques described in this document can allow a user suffering from OD undertake a treatment plan that is made interesting to the user by designing and planning the treatment as a fun exercise. For example, the VR environment that is presented to the user can be a designed as a VR game where the user has to go through multiple stages where during each stage of the game the user can complete an olfaction task to score some points. In some situations, the game can also be presented as a multi-user game where more than one user can participate and the users can collectively or independently try to score points as a competition.

The techniques and methods described in this specification can be used in different variations to as to customize the treatment as per the likings of each individual user thereby making more and more users undertake the treatment plan. For example, some users may prefer the treatment as a game that involves storytelling however other user may want the treatment as an examination where the users can score points based on their responses.

The techniques further include gathering VR experiences of multiple users and using those experiences to further enhance the treatment plan. For example, based on VR experiences that includes olfaction test results of multiple users, patterns can be identified that can be used to generate and update treatment protocol over time. For example, if majority of the users are able to perceive an aroma at a particular intensity at a particular distance from an object, it is highly likely that a new user will also be able to pervasive the aroma in the same conditions. If a user fails to detect the aroma it would indicate how the user's OD conditions differentiates from the rest of the users which might require further assistance during the treatment plan.

In general, one innovative aspect of the subject matter described in this specification can be embodied in methods including the operations of transmitting, to a client device, a first data indicating a first object from a plurality of objects and a first aroma associated with the first object for presentation to a user of the client device; receiving, from the client device, a user response that was provided by the user in response to the presentation of the first object and the first aroma and based on the user experience of perceiving the first aroma of the first object by the user; storing the user response in a database as an instance of a training dataset for the user; determining as output, a second data indicating a second object from a plurality of objects and a second aroma associated with the second object based on the user response; transmitting, to the client device, the second data indicating the second object and the second aroma for presentation to the user of the client device.

Other aspects include corresponding systems, apparatus, and computer programs to perform the actions of methods defined by instructions encoded on computer storage devices. These and other versions may optionally include one or more of the following features.

For instance, in some implementations, the method may further include displaying the respective object on a display screen of a client device wherein the display screen can support virtual reality (VR); dispersing the respective aroma associated to the respective object and displayed on the display screen of the client device using an aroma dispenser of the client device.

Methods can include displaying a plurality of objects in the VR space generated by the client device; dispersing the aroma associated to a particular object at an intensity level, wherein the intensity level is based on the user position with respect to the VR space and the distance of the user position in the VR space to the particular object in the VR space; changing the intensity level of the aroma based on the change in the user position in the VR space and change in the distance of the user position in the VR space to the particular object in the VR space; receiving a response from the user indicating a user selection of an object in the VR space; revealing the particular object to the user in the VR space and an indication of whether the object selected by the user is the same as the particular object.

Methods can include displaying to the user in the VR space a plurality of objects; receiving a response from the user indicating a selection of an object from the plurality of objects, wherein, in response to the user selection of an object, dispersing the aroma associated to the object; receiving a response from the user indicating a selection of two objects from the plurality of objects; and in response to selecting two objects from the plurality of objects, displaying to the user whether the two selected objects have the same aroma.

Methods can include the user response provided by the user in response to the presentation of the first object and the first aroma based on the user experience to include electrical activity of the brain of the user collected using one or more electrodes of the client device affixed to the scalp of the user wherein the electrical activity of the brain identifies brain activity in response to the user smelling the first object.

Methods can include the user response provided by the user in response to the presentation of the first object and the first aroma based on the user experience to include (1) an indication whether the user was able to perceive the first aroma, (2) an indication whether the user is able to associate the first object and the first aroma, and (3) a score provided by the user indicating the level of confidence the user has on the association of the first object and first aroma.

Methods can include identifying, the training dataset associated with the user of the client device; creating a new training sample for each user response received from the client device in response to the presentation of the first object and the first aroma wherein each training sample indicates (1) the first object, (2) the first aroma, (3) an indication whether the user was able to perceive the first aroma, (4) an indication whether the user is able to associate the first object and the first aroma, and (5) a score provided by the user indicating the level of confidence the user has on the association of the first object and first aroma.

Methods can further include identifying one or more users from among the plurality of users based on prior user responses; identifying for each of the one or more users, a respective training dataset; generating the data model based on the one or more identified training dataset that further includes: generating a rule-based data model that includes a set of rules that generates as output, the second data that indicates the second object and the second aroma; generating a machine learning data model that is trained on the one or more identified training datasets to generate as output, the second data that indicates the second object and the second aroma.

Particular embodiments of the subject matter described in this specification can be implemented so as to realize one or more of the following advantages. The techniques and methods described in this specification generates data points indicating user responses to different types of aroma. Patterns in such data is used to create a treatment plan for users suffering from OD. The techniques allow the users to participate in the treatment from either home or any location preferred by the user. The techniques further allow to change the treatment plan according to the user requirements so that the users can be provided with a custom user-specific treatment plan that will result in a faster recovery from OD. The treatment plan can be further customized or changed while the treatment is ongoing.

The techniques and methods implements state-of-the-art machine learning models and rule based model to learn the intricate relationships in the data that would generally go unnoticed. Use of such models to treat OD results in a faster recovery of users from OD. The techniques and methods are further implemented in a way that allows distribution of processing between servers implementing the treatment plan and VR headsets so as not bottleneck either one of them. The methods also allow generating of treatment plans ahead of time and downloaded on the VR headset so as to not use valuable computing resources when the user is undertaking the test or when the user is not connected to the internet.

The details of one or more embodiments of the subject matter described in this specification are set forth in the accompanying drawings and the description below. Other features, aspects, and advantages of the subject matter will become apparent from the description, the drawings, and the claims.

DETAILED DESCRIPTION

Figure 1:
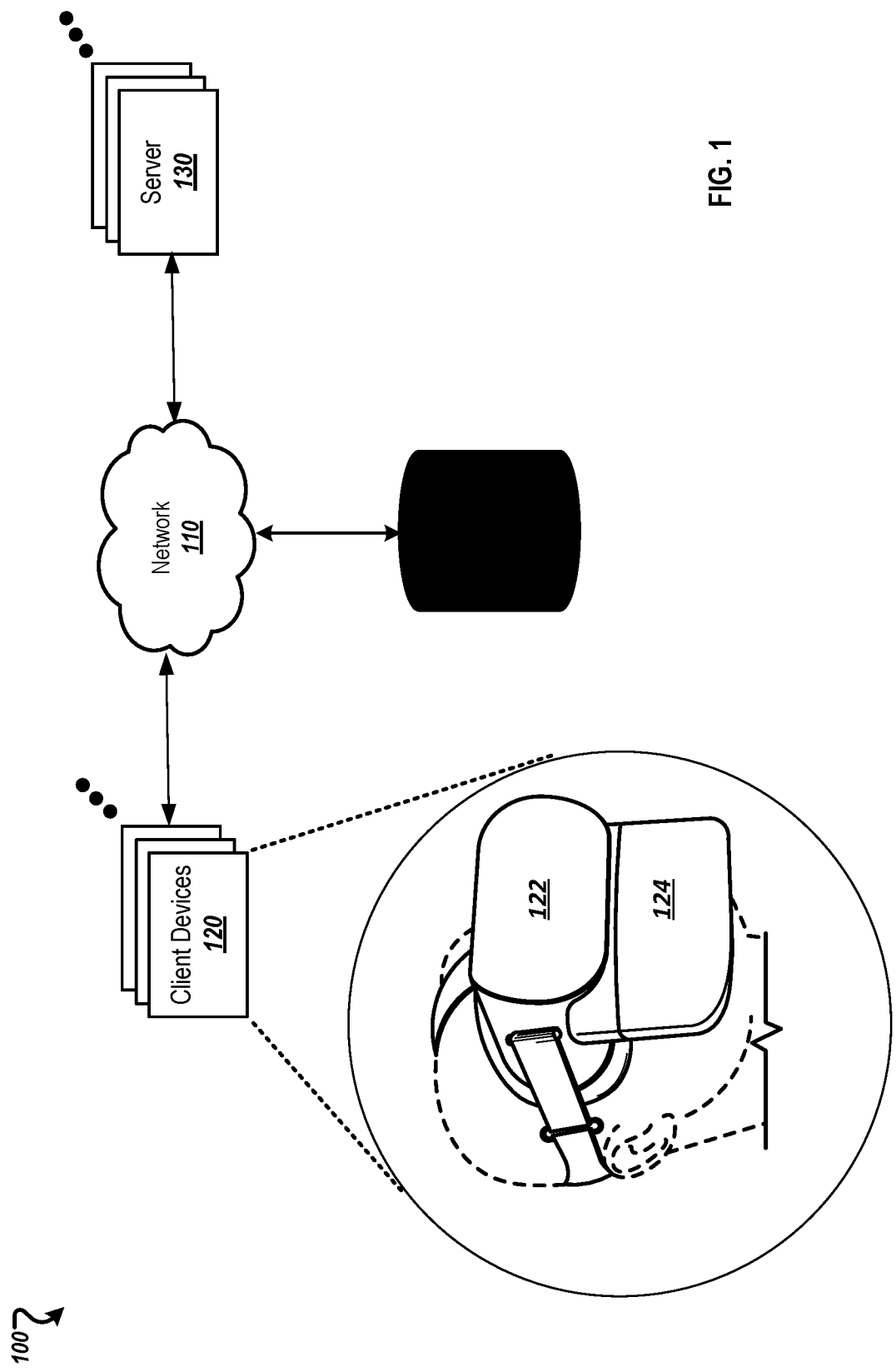
FIG. 1 is a block diagram of an example system that implements an online treatment service for users suffering from olfaction deficiency.

This specification generally describes a techniques and methods of generating OD treatment plan in a VR environment using a VR headset capable of dispersing aroma. The techniques and methods are implemented in a distributed environment where users undertake an OD treatment using VR headsets. The techniques described in this document can allow a user suffering from OD undertake a treatment plan that is made interesting to the user by designing and planning the treatment as a fun exercise. For example, the VR environment that is presented to the user can be a designed as a VR game where the user has to go through multiple stages where during each stage of the game the user can complete an olfaction task to score some points. In some situations, the game can also be presented as a multi-user game where more than one user can participate and the users can collectively or independently try to score points as a competition.

The techniques and methods described in this specification can be used in different variations to as to customize the treatment as per the likings of each individual user thereby making more and more users undertake the treatment plan. For example, some users may prefer the treatment as a game that involves storytelling however other user may want the treatment as an examination where the users can score points based on their responses. As an example, the user of the VR headset who prefers the treatment as a VR game can enter a VR room where the user has a flexibility of moving around. An example game in such a situation can include a user trying to perceive an aroma of an object such as a fruit in the room. As the user moves around the VR room, the intensity of the aroma changes based on the distance between the object and the user in the VR room. These techniques can allow the treatment plan to include more comprehensive gaming styles such as the user enacting a role of a detective who is trying to solve a mystery using the sense of smell. The techniques also allow the VR headset to record brain activity of the user in response to the user smelling an aroma. To enhance the training for each user by integrating electroencephalogram (EEG) and VR into the headset would to provide a greater degree of sensory immersion for the user of the VR headset The techniques further include gathering VR experiences of multiple users and using those experiences to further enhance the treatment plan. For example, based on VR experiences that includes olfaction test results of multiple users, patterns can be identified that can be used to generate and update treatment protocol over time. For example, if majority of the users are able to perceive an aroma at a particular intensity at a particular distance from an object, it is highly likely that a new user will also be able to pervasive the aroma in the same conditions. If a user fails to detect the aroma it would indicate how the user's OD conditions differentiates from the rest of the users which might require further assistance during the treatment plan.

The techniques further allow using the VR experiences to generate machine learning models to learn intricate relationships that may otherwise be undetected. The machine learning models can be further used to create a treatment plan that will prove to be more beneficial to the user. For example, the machine learning model can generate a sequence of aromas with different intensities that can result in the user identify aromas easily and at a faster rate thereby giving the users a sense of recovery.

It should be noted that the techniques and methods described in this document can also find applications in other areas such as gaming, education and engineering using virtual reality. For example, in the field of education, a teaching plan can be generated using the techniques and methods described here that allows for a better learning experience.

FIG. 1 is a block diagram of an example distributed environment 100 that can implement an OD treatment program. The environment 100 includes a network 110. The network 110 can include a local area network (LAN), a wide area network (WAN), the Internet or a combination thereof. The network 110 can also include any type of wired and/or wireless network, satellite networks, cable networks, Wi-Fi networks, mobile communications networks (e.g., 3G, 4G, and so forth) or any combination thereof. The network 104 can utilize communications protocols, including packet-based and/or datagram-based protocols such as internet protocol (IP), transmission control protocol (TCP), user datagram protocol (UDP), or other types of protocols. The network 104 can further include a number of devices that facilitate network communications and/or form a hardware basis for the networks, such as switches, routers, gateways, access points, firewalls, base stations, repeaters or a combination thereof. The network 110 connect client devices 120 such as VR headsets and one or more server systems 130.

Client devices 110 such as VR headsets are generally heads-up display (HUD) that allows users to interact with a VR which is an artificial computer generated environment in a first-person view (FPV). The VR headset can display digital content in the VR environment. As used throughout this document, the phrases "content" refer to a discrete unit of digital content or digital information (e.g., a video clip, audio clip, multimedia clip, image, text, or another unit of content). Content can be electronically stored in a physical memory device as a single file or in a collection of files, and content can take the form of video files, audio files, multimedia files, image files, or text files and include advertising information. Audio content may be presented by external devices (e.g., speakers) and/or devices that are internal to the VR headset (e.g., headphones).

VR headsets typically include an electronic display 122, a rendering apparatus that uses the electronic display to render digital content, an array of sensors (e.g., motion tracking sensors, head and eye tracking sensors and positional sensors) that keep track of the user motion and alignment with respect to the VR environment and the physical environment around the user. VR headsets are capable of communicating with other entities over the network 110. For example, VR headsets are capable of requesting, receiving and transmitting digital content over the network 110. VR headsets can also include an electronically controlled aroma dispenser 124 which is an atomizer sprayer that can spray one or more different perfumes at different intensities and time intervals to simulate one or more different types of aromas at different intensities.

In some implementations, the VR headset can also include one or more electrodes that can record brain activity of the user in response to the user smelling an aroma. The electrodes for example, can be attached to the scalp of the user using the VR headset. These electrodes can be inbuilt into the VR headset or they can be a separate attachment that can be installed on the VR headset using an interface.

The VR headset 120 typically includes a user application, such as VR based gaming applications and/or VR based applications provided by health care providers that can facilitate the sending and receiving of digital content and instructions over the network 110. The user application 126 is also the application that can use the components of the VR headset to present digital content to the user of the VR headset. The digital content can include images or a stream of images that forms the VR environment depicting a certain object or a place and the instructions when executed on the VR headset can release dispersing agent of a particular type or a particular configuration that is related to the object or place depicted in the virtual environment. For example, the digital content can depict a cup of coffee and the instructions causes release of dispersing agent that has a coffee like aroma. In another example, the digital content can depict a garden and the instructions causes release of dispersing agent that has a floral aroma.

If the user of the VR headset is suffering from OD and wants to engage into a series of tests to check the stage of OD that the user is suffering from, the user can select an application provided by a healthcare provider. The application can communicate with one or more servers that provide an online OD testing service. The application can exchange data over the network 110 to present digital content depicting objects to the user of the VR headset. The VR headset also disperses aroma that is associated to the depicted objects at different intensities to check if the user's olfactory sense is able to pick up the aroma. For example, the VR headset can present an object such as an "apple" in a VR environment and disperse the aroma of the "apple". If the user is not able to perceive the aroma which according to the VR headset and the OD testing service is the aroma of an "apple", the VR headset can increase the intensity of the aroma. If the user is able to perceive the aroma, the VR headset can decrease the intensity of the aroma. The iterative process can thereby allow the OD testing service to determine the severity of the OD.

As for another example, if the user of the VR headset is suffering from OD wants to undertake a treatment program to cure the OD, the user can select another application provided by a health care provider. The application can communicate with one or more servers 130 that provide an olfaction treatment program as an online service (referred to as an Online Treatment Service (OTS)) to allow the user to recognize aromas that the user was capable of before suffering from OD. The application can receive digital content depicting an object from the OTS along with instructions to release dispersing agent associated to the object to the user. After receiving the digital content and instructions, the application presents the object by displaying the digital content in the VR environment and executes instructions that results in releasing the dispersing agent. For example, the VR headset can present a digital content that depicts an "apple" and releases the aroma of an "apple". Similarly, the digital content can depict a cup of coffee and the instructions causes release of dispersing agent that has a coffee like aroma. In another example, the digital content can depict a garden and the instructions causes release of dispersing agent that has a floral aroma. The user of the VR headset can interact with the VR to indicate whether the user is able to perceive an aroma dispersed by the VR headset, and whether the user is able to conclude that the aroma is related to the object in the VR environment. The VR headset transmits the user interaction to the OTS and the OTS can present a next best alternative object and an associative aroma to the user. The OTS can determine the next best alternative object and the associated aroma based on historical data including user interactions and data collected from other users. The following description provides an in-depth view of the techniques and methods of implementing a treatment program.

The OTS is an online service that can be provided by a health care provider to manage and generate a treatment program for the users using servers 130. For example, the OTS can manage user profiles of the users enrolled into the treatment program including recording and updating data regarding ongoing treatment program of each user. For example, the OTS is responsible for managing the database 150 that stores user profiles, creating a training program for all users, customizing training program for one or more users etc. The OTS for example is also responsible for communicating with VR headsets of the users and transmit information such as digital content, data and instructions required to execute the treatment plan on the client side.

In some implementations, new users can join the olfaction training program provided by the OTS by registering with the provider of the OTS. The registration can include filling out an online form provided by the provider. For example, the new users can use a browser based application from a client device such as a PC, tablet or a smartphone to navigate to a webpage that includes the registration form via a universal resource locator (URL). After being presented with the registration form, the users can provide one or more details according to the registration form. For example, the users can provide their name, gender, email, mobile number etc. In some implementations, users can also provide details of their healthcare insurance one or more details regarding prior or current health conditions including basic physical attributes such as weight, height and age. Upon submission of the details, the OTS can generate a profile for the user and store it in a database 150. In some implementations, the OTS can add one or more other details to the user profile that for example can identify the user as a new user which can be leveraged by the service provider to teach and decide a training program best suited for beginners.

In some implementations, each user profile can also include user status data that can incorporates information such as log data indicating the training sessions that the user has undertaken. For example, the log data for a particular user can include times stamps of training sessions that the particular user of the VR headset took since the time the particular user enrolled into the olfaction training program. Log data can include information such as the software and hardware configuration of the VR headset including the application that is being executed in the VR headset, the geographical location of the VR headset and the quality of the network to which the VR headset is connected to.

In some implementations, user status data can also include historical data indicating digital content depicting different objects and the associated aromas that were presented to the user of the VR headset. For example, an instance of the log data includes the time stamps of a training session undertaken by a particular user. The corresponding historical data can include information such as the number of times the particular user of the VR headset was presented with digital content during the training session. Historical data can also include (or point to) the digital content that was presented to the user, the object depicted in the digital content, data identifying the associated aroma of the depicted object (and/or digital content), the intensity of the aroma etc.

In some implementations, user status data can also include user responses that were recorded by the VR headset and transmitted to the OTS. The user responses can sometimes be for example, user interactions that indicate can outcome of a positive or a negative identification of an object depicted in the VR environment based on the dispersed aroma, a score that indicates an association between the object and the dispersed aroma or brain activity recorded by the electrodes of the VR headset. For example, a user of a VR head set can be presented with one object that may be blurred or multiple objects that are not blurred. Simultaneously, the VR headset also releases dispersing agent that has a particular aroma. The user can then be asked to identify the object based on the particular aroma. In situations, when the object is blurred, the users can have options of providing their responses using a microphone of the VR headset. In situations, when the user is presented with multiple objects, the user can interact with the VR environment to select one or the objects as the user selection. In some implementations outcome of an identification of an object can be a score indicating the confidence that the user has while identifying the aroma.

If the VR headset includes electrodes to record brain activity, then user responses can also include fluctuations in electrical activity of the user's brain. The OTS can use the signals that identify olfaction to determine when aromas are being detected, independent of whether the patient is consciously aware or able indicate detection. It may also be used to detect fluctuations in intensity of the perceived aroma. This can be measured through changes both in activity location, and across time through electroencephalogram (EEG) methods of source localization and traditional signal analysis such as event related potential (ERP) or time-frequency analysis (TF).

In some implementations, the brain activity signals can also be used as additional input to machine learning models (described later) that can classify brain activity to determine the valence of the odor (pleasant or unpleasant) and the kind of odor detected. This can also provide additional data to help the machine learning models develop better precision in less time. In some implementations, the additional data can also be uploaded to data repositories to contribute to studies of population-level effects for improving general smell-disorder treatment protocols. Through measurement of brain signals, the system can adapt aroma training to the individual. For example, even if a user cannot subjectively identify different aromas, their brain may recognize that the odor is present, in response to which more aroma can be dispersed at a higher intensity or for a longer time interval until the user can subjectively detect the odor's presence.

In some implementations, the OTS can generate an OD treatment program that includes one or more sessions. Each session can include one or more olfaction tests where for each of the tests, the user suffering from OD is required smell and identify or correlate objects having similar aroma. In some implementations, the OTS and the application can implement the treatment program as a game to increase user's engagement with the treatment program. For example, the treatment session can include multiple olfaction tests where the user can score points by successfully identifying an object based on the aroma of the object.

In some implementations, the treatment plan can be made interesting by designing and planning the treatment as a fun exercise. For example, the VR environment that is presented to the user can be a designed as a VR game where the user has to go through multiple stages where during each stage of the game the user can complete an olfaction task to score some points. In some situations, the game can also be presented as a multi-user game where more than one user can participate and the users can collectively or independently try to score points as a competition.

In some implementations, the treatment session can include multiple olfaction tests based on a level of difficulty. For example, in some circumstances it can be assumed that it is easier to identify the aroma of coffee beans than identifying the aroma of some rare fruits. In such implementations, the OTS can select a difficulty level of an olfaction test based on a set of rules or a machine learning model trained based on the data collected by the OTS from all the users and their olfaction tests. For example, a rule based implementation of selecting the level of olfaction test can increment the level of difficulty based on a correct identification of an object based on the aroma of the object in the VR environment.

In some implementations, the OTS can record VR experiences of multiple users and can use experiences to further enhance the treatment plan. For example, based on VR experiences that includes olfaction test results of multiple users, patterns can be identified that can be used to generate and update treatment protocol over time. For example, if majority of the users are able to perceive an aroma at a particular intensity at a particular distance from an object, it is highly likely that a new user will also be able to pervasive the aroma in the same conditions. If a user fails to detect the aroma it would indicate how the user's OD conditions differentiates from the rest of the users which might require further assistance during the treatment plan.

In some implementations, when a user initiates a treatment session using the application of the VR headset, the VR headset communicates with the server 130 to notify the OTS to initiate a treatment session. In response, the OTS can access the user profile to analyze historical records of the user and the status of the user's training program to determine an object (referred to as a first object) for presentation to the user. For this the OTS can implement one or more rule-based models or machine learning models. The OTS can use the rule-based models and the machine learning models to determine based on the historical records, the previous treatment sessions undertaken by the user and how well the user performed in the olfaction tests in the previous sessions.

In some implementations, the OTS can analyze the data to explore patterns in the data collected from the users, the user profiles and test results to determine complex relationships that can be further exploited to improve the user experience and accelerate OD recovery. For example, the server can determine based on prior olfaction testing results, a sequence of olfaction tests that includes particular types of digital content representing an object or an environment and an associated aroma that results in an incremental triggering of user memory resulting in user remembering particular type of aromas prior to suffering from OD. The server after determining such patterns and due to a high success rates across multiple users, can create a testing plan for each user based on such patterns In some implementations, the OTS can determine patterns in the historical data that can be used to determine the olfaction tests of the recently initiated treatment session that the user is going to undertake. For example, assume that a particular user has undertaken four treatment sessions in the past and that each of the four treatment sessions include ten olfaction tests. Suppose the particular user was presented with citrus fruits of different types as objects in the VR environment and the corresponding citrus aroma ten times and out of those ten times the particular user failed nine times to correctly identify the citrus fruit based on the aroma. In such a situation the OTS can conclude that the particular user needs to improve OD for citrus aroma. Having concluded what kind of aroma needs to be presented to the user, the OTS can select objects that have a citrus aroma for presentation to the user.

As for another example, the OTS can determine based on historical data, a sequence of olfaction tests that includes particular types of digital content representing an object or an environment and an associated aroma that results in an incremental triggering of user memory resulting in user remembering particular type of aromas prior to suffering from OD. The OTS after determining such patterns and due to a high success rates across multiple users, can create a treatment program for each user.

As for another example, the OTS can generate one or more groups of users based on the user profiles and historical data. For example, the OTS can generate groups of users having one or more similar characteristics. For example, the OTS can create a user group that include only those users who have completed a certain number of training sessions. As for another example, the OTS can create a user group that includes users who for example, can correctly identify a particular aroma. The OTS can determine a sequence of olfaction tests based on such user groups. For example, a user in a particular group is likely to make similar mistakes during an olfaction test as other member of the particular group. Hence the user of the particular group should be undertake the same olfaction test based on the assumption that the user is similar to other members of the particular group and taking the test will make the user identify aromas not known the user.

In some implementations, to determine which kind or type of object should be presented to the user, the OTS can also implement one or more machine learning models to model the progression of the user's treatment. The machine learning models implemented by the OTS can include training parameters that can be trained on historical data to predict objects that when presented to the user will improve user's OD by progressively making the user identify different aromas that the user was previously familiar with.

In some implementations, the one or more machine learning models implemented by the OTS are configured to receive as input information from the user profile, user status data and historical data. For example, one of the machine learning models can be a neural network model that includes multiple neural network layers and each neural network layer can include multiple training parameters. The neural network can receive as input information from user profile include for example, age, gender and the date from when the user started showing symptoms of OD. The neural network can also receive as input information from one or more previous olfaction tests. For example, the object presented to the user, the user response etc. the neural network can also be configured to receive user group characteristics as input. The neural network model can process the input and generate as output a prediction indicating an object that can be presented to the user in the forthcoming olfaction test. Though the above example has been explained using a neural network model, the OTS can implement any machine learning model known in the art. For example, clustering, support vector machines (SVM).

The machine learning models implemented by the OTS can be trained on a training dataset that can be extracted from the user profile and user status data. For example, the training dataset can include training samples of multiple users where the training samples can include features such as gender, age, prior olfaction tests and results, score and electrical brain activity. In some implementations, the training dataset can also be a time-series that includes multiple training samples for multiple users sorted based on the users and the time of the olfaction tests.

Upon determination of the first object, the OTS can select digital content (referred to as first data) depicting the first object and instructions for releasing dispersing agent that has an aroma (referred to as a first aroma) of the first object. The first data and the first aroma is transmitted to the VR headset using the network 110. In some implementations, the VR headset after receiving the first data and the first aroma, presents the digital content depicting the first object in VR using the display screen of the VR headset and executes the instructions to release the first aroma.

In some implementation, the OTS can provide additional instructions to the application of the VR headset to implement different strategies and/or methods to present the first object and the first aroma in the VR headset. The OTS can also specify what type of response is expected from the user of the VR headset in response to presentation of the first object and the first aroma. For example, the OTS can provide additional instructions to the application to present the first object and disperse the first aroma simultaneously along with an option that the user can select suggesting "right" and "wrong". The user can see the first object in the VR and guess whether the first aroma is associated with the first object. Depending upon this guess, the user can select "right" or "wrong" in the VR. For example, the user can use external controllers or an eyeball tracking sensor in the VR headset to select an option. In some implementations, the OTS can also ask the user via the application of the VR headset to provide a score for the user's selection indicating the confidence the user has on the selection. For example, the OTS can instruct the application of the VR headset to present a scale in the VR environment and the user can select a score value from the scale by gazing at the score value on the scale.

In another example, the OTS can provide additional instructions to the application to present the first object and disperse the first aroma such that when the first object is presented, the image of the first object is blurred. In such a situation the user can be further instructed to identify the first object just based on the first aroma and provide the name of the first object as speech using the microphone of the VR headset. In such a situation, the user can also be provided with an option of hint, wherein the user of the VR headset can reduce the blurriness of the first object. By reducing the blurriness of the first object and by smelling the first aroma, the user of the VR headset can identify the first object. As for another example, the OTS can provide additional instructions to the application to increase the intensity of the first aroma to help the user guess whether the first aroma is associated to the first object that is presented by the VR headset. Few of these strategies are explained further with reference to FIG. 2.

Figure 2:
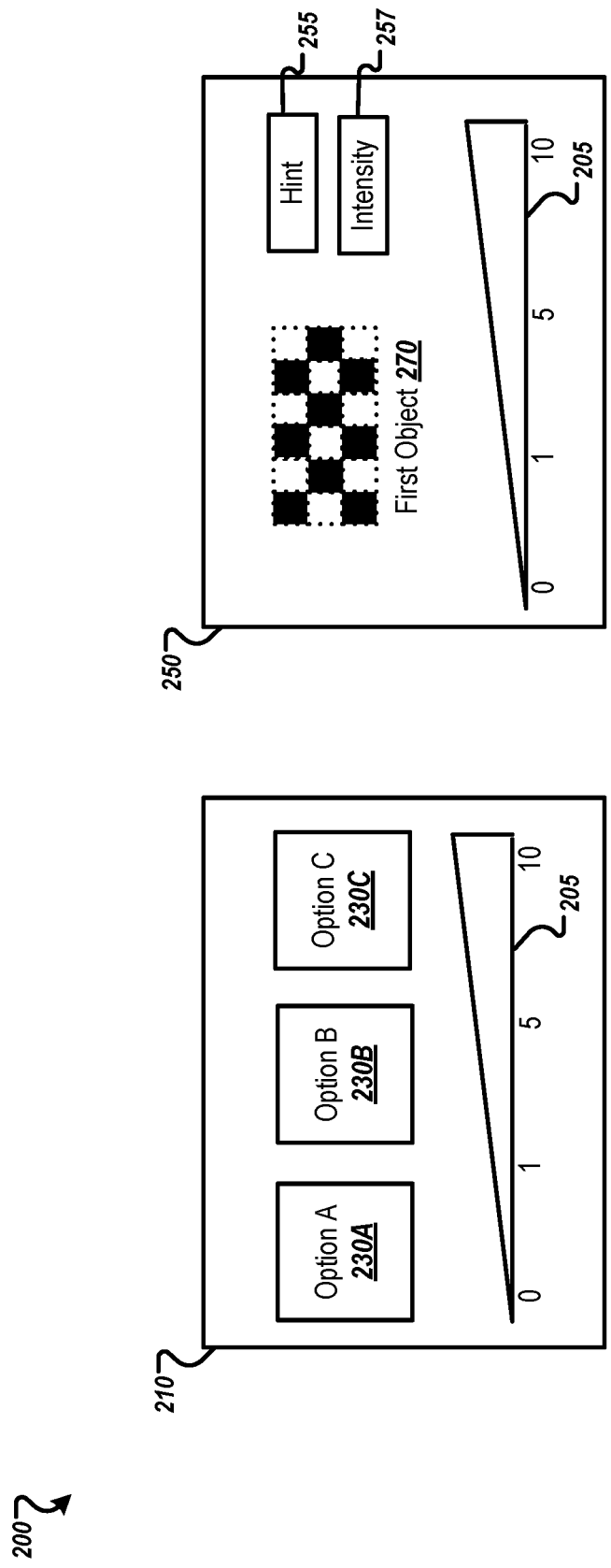
FIG. 2 is a block diagram that illustrates two strategies of presenting objects in virtual reality.

FIG. 2 is a block diagram that illustrates two strategies of presenting objects in VR. The two strategies are depicted as 210 and 250. For example, 210 represents a strategy, where a first object 230A is presented in the VR along with two other objects 230B and 230C. The user of the VR headset, after perceiving the first aroma, can select one of the objects from the multiple objects 230A-C and scores the user's selection using the scale 205. In the second strategy, a first object 270 is blurred by the application while presenting in the VR environment. The user can guess the first object 270 and provide a response using the microphone of the VR headset. If the user is unsure, the user can select the option 255 to reduce the blurring of the image 270 or the option 257 to increase the intensity of the first aroma.

In some implementations, the application after receiving the user response, can transmit the user response to the OTS of the server 130. Prior to transmitting the user response to the OTS, the application can analyze the user response and transmit either the final user selection or the final result of the user selection. For example, if the user provided the response using the microphone of the VR headset, the application can convert audio data of the microphone to textual data. In another example, the application can analyze the user response to determine whether the user selection of the first object was correct. In such a situation the application can transmit a binary value to the OTS where "1" can indicate that the user's response was correct and "0" can indicate that the user's response was wrong. Note that this reduces network traffic and reduces computational load on the server 130.

In some implementations, the OTS after receiving the user response can update the user status data based on the first object, the first aroma and the user response. For example, the OTS can create a new entry in the historical data indicating that the first object and the first aroma was presented to the user and that the user correctly identified the first object and vice-versa and the score provided by the user.

In some implementations, the OTS after receiving the user response, can determine another object (referred to as a second object) that should be presented to the user in the same training session. To determine the second object, the OTS can again process historical data including the first object, the first aroma and the user response using the one or more machine learning models to generate the second object. Upon determination of the second object, the OTS can select digital content (referred to as second data) depicting the second object and instructions for releasing dispersing agent that has an aroma (referred to as a second aroma) like the second object. The second data and the second aroma is transmitted to the VR headset using the network 110. Note that the OTS can also use techniques discussed with reference to determining the first data and the first aroma for presentation on the VR headset.

In some implementations, the olfaction tests may require the user to move in the VR environment. This allows the OTS to generate a more immersive olfaction test in VR environment that the user can enjoy. For example, the OTS can create an olfaction test by creating a three dimensional virtual room in the VR environment that include multiple objects. In such a scenario, the OTS can transmit instructions to the VR headset for the release of dispersing agent at a low intensity thereby simulating that the source of the aroma is at a distance. The user can then move in the three dimensional virtual room. As the user moves closer a particular object among the multiple objects that is the source of the aroma in the three dimensional virtual room, VR headset can update the OTS about the user's co-ordinates inside the three dimensional virtual room. Depending upon how close the user is to the particular object in the three dimensional virtual room, the OTS can transmit instructions to alter the intensity of the release of the dispersing agent thereby creating an illusion for the user of moving closer or farther away from the particular object.

Continuing with the above example, the user of the VR headset continues to move inside the three dimensional virtual room. When the user is selects an object from among the multiple objects in the room, the user selection is recorded as a response that transmitted to the OTS. The OTS after receiving the user response, evaluates the response to determine whether the user selection is correct. The OTS can then transmit further instructions to the VR headset to notify the user about whether the selected object is the particular object. If the selected object is not the particular object, the user can continue with the test.

Using such methods the OTS can also create a training session as a game with a storyline that can be depicted using a video or multiple images in the VR environment. For example, the training session can include creating a three dimensional virtual room in the VR environment that can be depicted as a crime scene. The user can move within the room and where the user can play a role of a detective. In this example, the user can uncover secret hidden in the room by undertaking different olfaction tests presented to the user as a part of the story. For example, the OTS can transmit instructions to release a dispersing agent of a particular aroma at very low intensity. Simultaneously the digital content transmitted and presented in the VR headset will generate an experience of the aroma of the dispersing agent coming from a distance inside the virtual room. The user can move inside the virtual room to uncover the reason behind the aroma. As the user moves inside the virtual room the OTS can transmit instructions to alter the intensity of the dispersing agent that will alter the intensity of aroma there by proving the user an experience of moving towards or away from the source of the aroma.

In some implementations, the OTS can create olfaction tests in which the user can compare two or more objects among the multiple objects based on the aroma of the two or more objects. Similar to the example explained above, the user can move around in a three dimensional virtual room that includes multiple objects where each of the multiple object has an associated aroma. In this example, the user can select two or more objects from among the multiple objects that according to the user have a similar aroma. The VR headset after recording the user selection, transmits the user response to the OTS. The OTS evaluates the user response and transmits instructions to the VR headset to notify the user about whether the selected objects have similar aroma. If the selected objects do not have the similar aroma, the user can continue with the test.

In some implementations, the OTS can create a training session that includes multiple olfaction tests where during each test the user can be presented with the same object but with different aroma intensities. For example, if the OTS determines that a user is not able to perceive a particular type of aroma, the OTS can generate a treatment session where the user can be presented with an object that has the particular type of aroma. While presenting the object in the VR environment, the OTS can transmit instructions to the VR headset to alter the intensity of the aroma dispersed by the aroma dispenser. For example, the VR headset can dispense the aroma at a specific intensity. If the user of the VR headset is not able to perceive the aroma, the VR headset can increase the intensity of the aroma. On the contrary, if the user of the VR headset is able to perceive the aroma, the VR headset in decrease the intensity of the aroma dispersed by the aroma dispenser. By varying the intensity of the aroma, the user is expected to be able to perceive aroma at specific intensities thereby improving the user's sense of olfaction.

The techniques and methods described above can be used in different variations to as to customize the treatment as per the likings of each individual user thereby making more and more users undertake the treatment plan. For example, some users may prefer the treatment as a game that involves storytelling however other user may want the treatment as an examination where the users can score points based on their responses.

Figure 3:
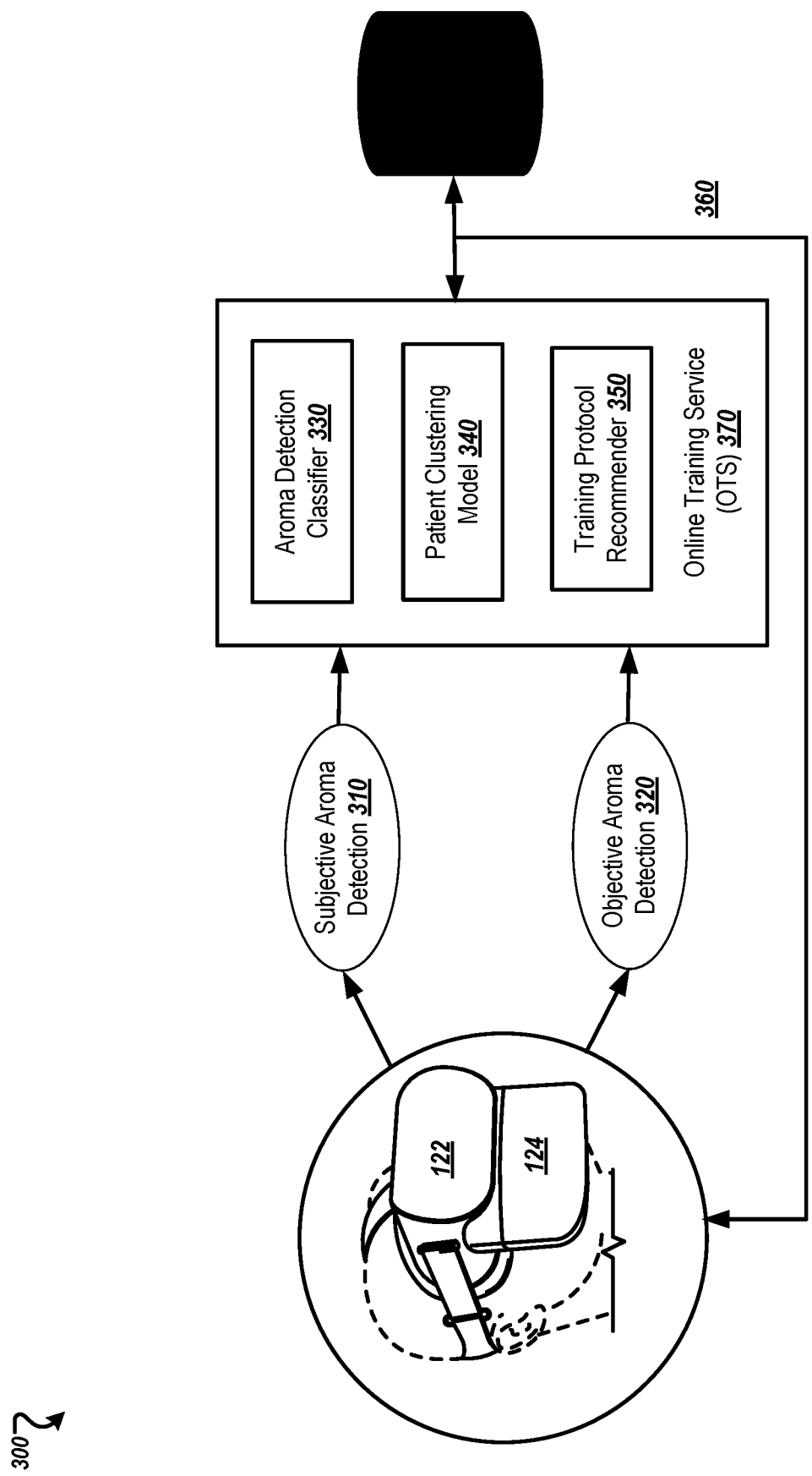
FIG. 3 is a block diagram that illustrates an example of an online treatment service that utilizes brain activity of the user of the VR headset.

FIG. 3 is a block diagram illustrating an example OTS 370 that utilizes brain activity of the user of the VR headset. Operations explained with reference to FIG. 3 can be implemented, for example, by the VR headset and one or more servers executing the OTS 370. Operations can be implemented as instructions stored on one or more computer readable media which may be non-transitory, and execution of the instructions by one or more data processing apparatus can cause the one or more data processing apparatus to perform the operations.

As seen in FIG. 3, the VR headset 120 receives instructions 360 from the OTS 370. The instructions 360 includes data of the VR environment presented by the display 122 of the VR headset and data related to the aroma that is dispersed by the aroma dispenser 124. After dispersing the aroma and presenting the VR environment to the user of the VR headset, the user tries to identify the aroma. For example, the user of the VR headset can detect aroma using the sense of olfaction (referred to as subjective aroma detection 310). It is also possible that the user of the VR headset is unable to detect the dispersed aroma however VR headset is able to detect fluctuations in electrical activity of the user's brain using EEG methods (referred to as objective aroma detection 320).

After detecting the dispersed aroma, the indication of whether the aroma was detected by the user of the VR headset is transmitted to the OTS 370. For example, in case of subjective aroma detection 310, the user of the VR headset can provide an indication by interacting with the VR environment. In case of objective aroma detection, the VR headset can either process the user's brain signals to generate an indication of whether the user actually detected any aroma or transmit the brain signals to the OTS 370. In the latter case, the OTS 370 can process the brain signals to generate the indication of whether the user actually detected any aroma.

In some implementations, the OTS 370 can implement an aroma detection classifier 330 that is trained process the indications of whether the aroma was detected by the user of the VR headset and classify whether the user was actually able to detect any aroma. For example, the user may subjectively fail to detect the dispersed aroma but objectively be able to detect the aroma. After classifying the user, the OTS 370 can use a patient clustering model 340 to classify the patient into one or the multiple categories of users enrolled with the OTS 370. For example, users that were objectively able to detect aroma but unable to detect aroma subjectively can be classified as a group of users with similar characteristics. The users can further be classified in sub-categories based on user profile.

In some implementations, the OTS 370 can use a training protocol recommender 350 to process user profile of the user of the VR headset along with the outputs of the aroma detection classifier 330 and the patient clustering model 340 to generate a recommendation for aroma and VR environment for a subsequent olfaction test for the user of the VR headset. The recommended olfaction test that includes instructions for dispersing aroma and presenting a VR environment that is transmitted back to the VR headset of the user. In some implementations, the outputs of the aroma detection classifier 330, the patient clustering model 340 along with the indications of aroma detection (including subjective and objective aroma detection) is stored in the profile database 152.

Figure 4:
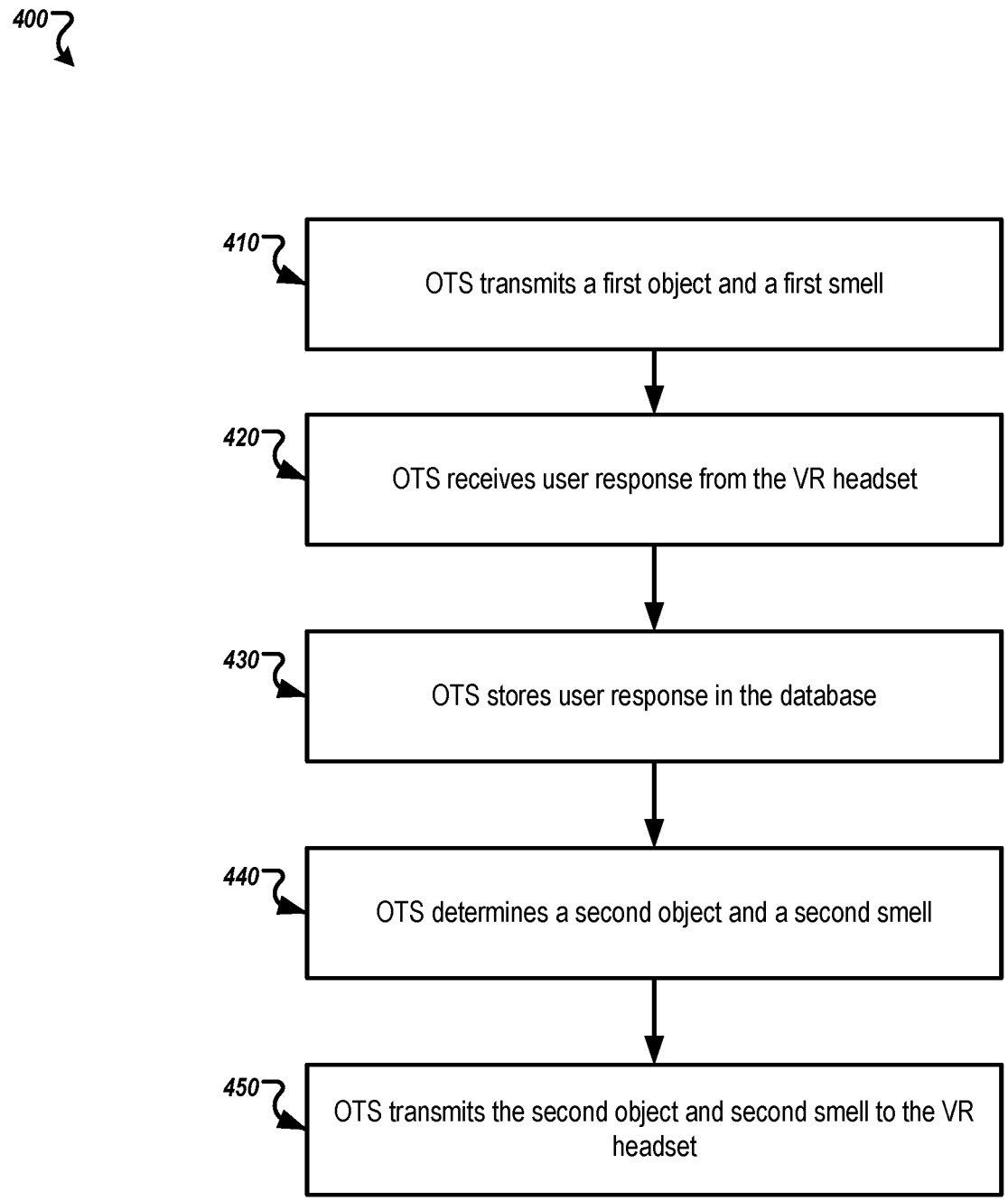
FIG. 4 is a flow diagram of an example process of the olfaction treatment service.

FIG. 4 is a flow diagram of an example process 400 of the olfaction training program. Operations of process 400 are described below as being performed by the components of the system described and depicted in FIGS. 1-3. Operations of the process 400 are described below for illustration purposes only. Operations of the process 400 can be performed by any appropriate device or system, e.g., any appropriate data processing apparatus. Operations of the process 400 can also be implemented as instructions stored on a non-transitory computer readable medium. Execution of the instructions cause one or more data processing apparatus to perform operations of the process 400.

The OTS transmits a first object and a first aroma to the VR headset (410). For example, when a user initiates a treatment session using the application of the VR headset, the VR headset communicates with the server 130 to notify the OTS to initiate a treatment session. In response, the OTS can access the user profile to analyze historical records of the user and the status of the user's training program to determine an object (referred to as a first object) for presentation to the user. For this the OTS can implement one or more rule-based models or machine learning models. The OTS can use the rule-based models and the machine learning models to determine based on the historical records, the previous treatment sessions undertaken by the user and how well the user performed in the olfaction tests in the previous sessions. For example, the machine learning models implemented by the OTS can include training parameters that can be trained on historical data to predict objects that when presented to the user will improve user's OD by progressively making the user identify different aromas that the user was previously familiar with Upon determination of the first object, the OTS can select digital content (referred to as first data) depicting the first object and instructions for releasing dispersing agent that smells like a first aroma like the first object. The first data and the first aroma is transmitted to the VR headset using the network 110. In some implementations, the VR headset after receiving the first data and the first aroma, presents the digital content depicting the first object in VR using the display screen of the VR headset and executes the instructions to release the first aroma.

In some implementation, the OTS can provide additional instructions to the application of the VR headset to implement different strategies and/or methods to present the first object and the first aroma in the VR headset. The OTS can also specify what type of response is expected from the user of the VR headset in response to presentation of the first object and the first aroma. For example, the OTS can provide additional instructions to the application to present the first object and disperse the first aroma simultaneously along with an option that the user can select suggesting "right" and "wrong".

The OTS receives user response from the VR headset (420). The OTS can provide additional instructions to the application of the VR headset to implement different strategies and/or methods to present the first object and the first aroma in the VR headset. The OTS can also specify what type of response is expected from the user of the VR headset in response to presentation of the first object and the first aroma. For example, the OTS can provide additional instructions to the application to present the first object and disperse the first aroma simultaneously along with an option that the user can select suggesting "right" and "wrong". The user can see the first object in the VR and guess whether the first aroma is associated with the first object. Depending upon this guess, the user can select "right" or "wrong" in the VR. For example, the user can use external controllers or an eyeball tracking sensor in the VR headset to select an option. In some implementations, the OTS can also ask the user via the application of the VR headset to provide a score for the user's selection indicating the confidence the user has on the selection. For example, the OTS can instruct the application of the VR headset to present a scale in the VR environment and the user can select a score value from the scale by gazing at the score value on the scale.

The application after receiving the user response, can transmit the user response to the OTS of the server 130. Prior to transmitting the user response to the OTS, the application can analyze the user response and transmit either the final user selection or the final result of the user selection. For example, if the user provided the response using the microphone of the VR headset, the application can convert audio data of the microphone to textual data. In another example, the application can analyze the user response to determine whether the user selection of the first object was correct. In such a situation the application can transmit a binary value to the OTS where "1" can indicate that the user's response was correct and "0" can indicate that the user's response was wrong. Note that this reduces network traffic and reduces computational load on the server 130.

The OTS stores user response in the database (430). For example, the OTS after receiving the user response can update the user status data based on the first object, the first aroma and the user response. For example, the OTS can create a new entry in the historical data indicating that the first object and the first aroma was presented to the user and that the user correctly identified the first object and vice-versa and the score provided by the user.

The OTS determines a second data and a second aroma (440). For example, the OTS after receiving the user response, can determine another object (referred to as a second object) that should be presented to the user in the same training session. To determine the second object, the OTS can again process historical data including the first object, the first aroma and the user response using the one or more machine learning models to generate the second object. Upon determination of the second object, the OTS can select digital content (referred to as second data) depicting the second object and instructions for releasing dispersing agent that smells like a second aroma like the second object. The second data and the second aroma is transmitted to the VR headset using the network 110. The OTS can also use the rule-based techniques and the machine learning models used to determine the first data and first aroma for determining the second data and the second aroma.

The OTS transmits the second object and a second aroma to the VR headset (450). For example, after determining the second object, the OTS can select digital content (referred to as second data) depicting the second object and instructions for releasing dispersing agent that smells like a second aroma like the second object. The second data and the second aroma is transmitted to the VR headset using the network 110. In some implementations, the VR headset after receiving the second data and the second aroma, presents the digital content depicting the second object in VR using the display screen of the VR headset and executes the instructions to release the second aroma.

Figure 5:
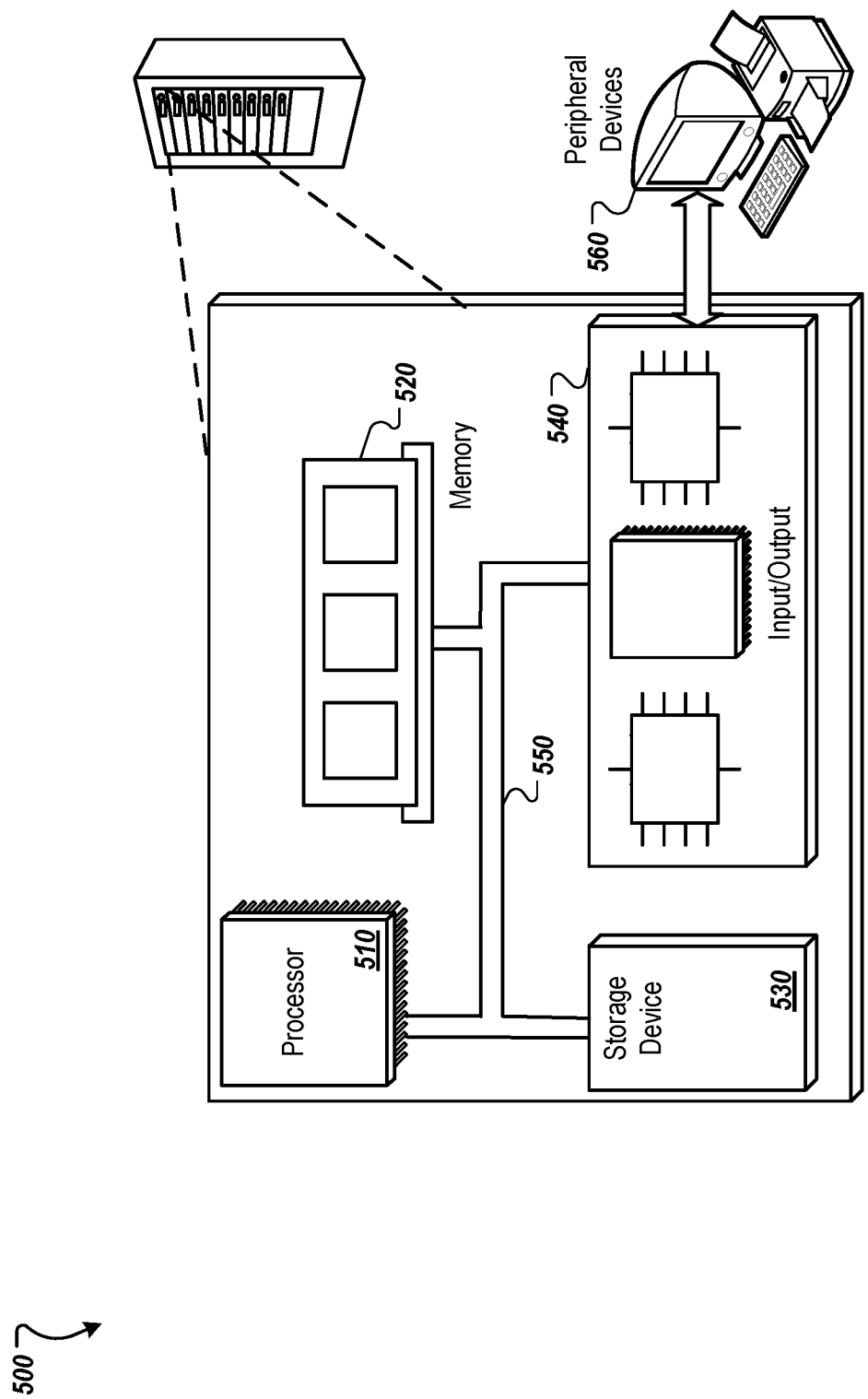
FIG. 5 is a block diagram of an example computer system.

FIG. 5 is a block diagram of an example computer system 500 that can be used to perform operations described above. The system 500 includes a processor 510, a memory 520, a storage device 530, and an input/output device 540. Each of the components 510, 520, 530, and 540 can be interconnected, for example, using a system bus 550. The processor 510 is capable of processing instructions for execution within the system 500. In one implementation, the processor 510 is a single-threaded processor. In another implementation, the processor 510 is a multi-threaded processor. The processor 510 is capable of processing instructions stored in the memory 520 or on the storage device 530.

The memory 520 stores information within the system 500. In one implementation, the memory 520 is a computer-readable medium. In one implementation, the memory 520 is a volatile memory unit. In another implementation, the memory 520 is a non-volatile memory unit.

The storage device 530 is capable of providing mass storage for the system 400. In one implementation, the storage device 530 is a computer-readable medium. In various different implementations, the storage device 530 can include, for example, a hard disk device, an optical disk device, a storage device that is shared over a network by multiple computing devices (e.g., a cloud storage device), or some other large capacity storage device.

The input/output device 540 provides input/output operations for the system 500. In one implementation, the input/output device 540 can include one or more of a network interface devices, e.g., an Ethernet card, a serial communication device, e.g., and RS-232 port, and/or a wireless interface device, e.g., and 802.11 card. In another implementation, the input/output device can include driver devices configured to receive input data and send output data to peripheral devices 560, e.g., keyboard, printer and display devices. Other implementations, however, can also be used, such as mobile computing devices, mobile communication devices, set-top box television client devices, etc.

Although an example processing system has been described in FIG. 5, implementations of the subject matter and the functional operations described in this specification can be implemented in other types of digital electronic circuitry, or in computer software, firmware, or hardware, including the structures disclosed in this specification and their structural equivalents, or in combinations of one or more of them.

An electronic document (which for brevity will simply be referred to as a document) does not necessarily correspond to a file. A document may be stored in a portion of a file that holds other documents, in a single file dedicated to the document in question, or in multiple coordinated files.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage media (or medium) for execution by, or to control the operation of, data processing apparatus. Alternatively, or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some embodiments, a server transmits data (e.g., an HTML page) to a client device (e.g., for purposes of displaying data to and receiving user input from a user interacting with the client device). Data generated at the client device (e.g., a result of the user interaction) can be received from the client device at the server.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A computer-implemented method for aroma training, comprising:
generating training data sets for training a machine learning model to identify one of a plurality of objects to present after initially presenting another one of the plurality of objects to incrementally trigger increased user perception of aromas by users that are suffering from olfactory disfunction, the training data sets each including data indicating (i) another one of the plurality of objects that was initially presented to one of the users, (ii) one of the plurality of objects that were presented to the one of the users after initially presenting the another one of the plurality of objects, (iii) and electrical brain activity data of the one of the users that reflects an extent to which presentation of the aromas of the one of the plurality of objects and the another one of the plurality of objects created fluctuations in electrical activity of a brain of the one of the users when the one of the plurality of objects and the another one of the plurality of object were presented;

training the machine learning model in such a way that the aromas of the another one of the plurality of objects is followed in sequence by the aromas of the one of the plurality of objects, to predict objects from a plurality of objects based on the aromas;

transmitting, to a client device, a first data indicating a first object from the plurality of objects and instructions to disperse a first aroma associated with the first object for presentation to a user of the client device;

receiving, from the client device, a user response that was provided by the user in response to the presentation of the first object and the first aroma, the user response comprising electrical brain activity data of the user that reflects an extent to which an aroma of the first object was perceived;

storing the user response in a database as an instance of a training dataset for the user;

identifying, based on the user response, a second object from the plurality of objects using the trained machine learning model;

determining the aroma of the second object based on the electrical brain activity data of the one of the users; and transmitting, to the client device, the second data indicating the second object and instructions to disperse the second aroma for presentation to the user of the client device.

2. The computer-implemented method of claim 1, wherein presenting the first and the second data by the client device comprises:

displaying the respective object on a display screen of a client device wherein the display screen can support virtual reality (VR);

dispersing the respective aroma associated to the respective object and displayed on the display screen of the client device using a aroma dispenser of the client device.

3. The computer-implemented method of claim 1, comprising:

displaying a plurality of objects in the VR space generated by the client device;

dispersing the aroma associated to a particular object at an intensity level, wherein the intensity level is based on the user position with respect to the VR space and the distance of the user position in the VR space to the particular object in the VR space; and changing the intensity level of the aroma based on the change in the user position in the VR space and change in the distance of the user position in the VR space to the particular object in the VR space;

receiving a response from the user indicating a user selection of an object in the VR space;

revealing the particular object to the user in the VR space and an indication of whether the object selected by the user is the same as the particular object.

4. The computer-implemented method of claim 3, comprising:

displaying to the user in the VR space the plurality of objects, receiving a response from the user indicating a selection of an object from the plurality of objects, wherein, in response to the user selection of the object, dispersing the aroma associated to the object; and receiving a response from the user indicating a selection of two objects from the plurality of objects; and in response to selecting two objects from the plurality of objects, displaying to the user whether the two selected obj ects have the same aroma.

5. The computer-implemented method of claim 4, wherein the user response provided by the user in response to the presentation of the first object and the first aroma is collected using one or more electrodes of the client device affixed to the scalp of the user wherein the electrical activity of the brain identifies brain activity in response to the user smelling the first object.

6. The computer-implemented method of claim 1, wherein the user response provided by the user in response to the presentation of the first object and the first aroma based on the user experience comprises (1) an indication whether the user was able to perceive the first aroma, (2) an indication whether the user is able to associate the first object and the first aroma, and (3) a score provided by the user indicating the level of confidence the user has on the association of the first object and first aroma.

7. A system for aroma training, comprising one or more processors and one or more non-transitory computer readable media that store instructions which, when executed by the one or more processors, cause the one or more processors to perform operations comprising:

generating training data sets for training a machine learning model to identify one of a plurality of objects to present after initially presenting another one of the plurality of objects to incrementally trigger increased user perception of aromas by users that are suffering from olfactory disfunction, the training data sets each including data indicating (i) another one of the plurality of objects that was initially presented to one of the users, (ii) one of the plurality of objects that were presented to the one of the users after initially presenting the another one of the plurality of objects, (iii) and electrical brain activity data of the one of the users that reflects an extent to which presentation of the aromas of the one object and the another one of the objects created fluctuations in electrical activity of a brain of the one of the users when the one of the plurality of object and the another one of the plurality of objects were presented;

training the machine learning model in such a way that the aromas of the another one of the plurality of objects is followed in sequence by the aromas of the one of the plurality of objects, to predict objects from the plurality of objects based on the aromas;

transmitting, to a client device, a first data indicating a first object from the plurality of objects and instructions to disperse a first aroma associated with the first object for presentation to a user of the client device;

receiving, from the client device, the user response that was provided by the user in response to the presentation of the first object and the first aroma, the user response comprising electrical brain activity data of the user that reflects an extent to which an aroma of the first object was perceived;

storing the user response in a database as an instance of a training dataset for the user;

identifying, based on the user response, a second object from the plurality of objects using the trained machine learning model;

determining a second aroma that is associated with the second object based on the electrical brain activity data of the one of the users;

transmitting, to the client device, the second data indicating the second object and instructions to disperse the second aroma for presentation to the user of the client device.

8. The system of claim 7, wherein presenting the first and the second data by the client device comprises:

displaying the respective object on a display screen of a client device wherein the display screen can support virtual reality (VR); and
dispersing the respective aroma associated to the respective object and displayed on the display screen of the client device using an aroma dispenser of the client device.

9. The system of claim 7, wherein the operations comprise:
displaying a plurality of objects in the VR space generated by the client device;
dispersing the aroma associated to a particular object at an intensity level, wherein the intensity level is based on the user position with respect to the VR space and the distance of the user position in the VR space to the particular object in the VR space;
changing the intensity level of the aroma based on the change in the user position in the VR space and change in the distance of the user position in the VR space to the particular object in the VR space;
receiving a response from the user indicating a user selection of an object in the VR space; and
revealing the particular object to the user in the VR space and an indication of whether the object selected by the user is the same as the particular object.

10. The system of claim 9, wherein the operations comprise:
displaying to the user in the VR space the plurality of objects;
receiving a response from the user indicating a selection of an object from the plurality of objects,
wherein, in response to the user selection of an object, dispersing the aroma associated to the object;
receiving a response from the user indicating a selection of two objects from the plurality of objects; and
in response to selecting two objects from the plurality of objects, displaying to the user whether the two selected objects have the same aroma.

11. The system of claim 10, wherein the user response provided by the user in response to the presentation of the first object and the first aroma is collected using one or more electrodes of the client device affixed to the scalp of the user wherein the electrical activity of the brain identifies brain activity in response to the user smelling the first object.

12. The system of claim 7, wherein the user response provided by the user in response to the presentation of the first object and the first aroma based on the user experience comprises (1) an indication whether the user was able to perceive the first aroma, (2) an indication whether the user is able to associate the first object and the first aroma, and (3) a score provided by the user indicating the level of confidence the user has on the association of the first object and first aroma.

13. A non-transitory computer readable medium storing instructions that, when executed by one or more data processing apparatus, cause the one or more data processing apparatus to perform operations comprising:
generating training data sets for training a machine learning model to identify one of a plurality of objects to present after initially presenting another one of the plurality of objects to incrementally trigger increased user perception of aromas by users that are suffering from olfactory disfunction, the training data sets each including data indicating (i) another one of the plurality of objects that was initially presented to one of the users, (ii) one of the objects that were presented to the one of the users after initially presenting the another one of the plurality of objects, (iii) and electrical brain activity data of the one of the users that reflects an extent to which presentation of the aromas of the one of the plurality of objects and the another one of the objects created fluctuations in electrical activity of a brain of the one of the users when the one object and the another object were presented;
training the machine learning model in such a way that the aromas of the another one of the plurality of objects is followed in sequence by the aromas of the one of the objects, to predict objects from a plurality of objects based on the aromas;
transmitting, to a client device, a first data indicating a first object from the plurality of objects and instructions to disperse a first aroma associated with the first object for presentation to a user of the client device;
receiving, from the client device, a user response that was provided by the user in response to the presentation of the first object and the first aroma, the user response comprising electrical brain activity data of the user that reflects an extent to which an aroma of the first object was perceived;
storing the user response in a database as an instance of a training dataset for the user;
identifying, based on the user response, a second object from the plurality of objects using the trained machine learning model;
determining a second aroma that is associated with the second object based on the electrical brain activity data of the one of the users; transmitting, to the client device, the second data indicating the second object and instructions to disperse the second aroma for presentation to the user of the client device.

14. The non-transitory computer readable medium of claim 13, wherein presenting the first and the second data by the client device comprises:
displaying the respective object on a display screen of a client device wherein the display screen can support virtual reality (VR); and
dispersing the respective aroma associated to the respective object and displayed on the display screen of the client device using an aroma dispenser of the client device.

15. The non-transitory computer readable medium of claim 13, wherein the operations comprise:
displaying a plurality of objects in the VR space generated by the client device;
dispersing the aroma associated to a particular object at an intensity level, wherein the intensity level is based on the user position with respect to the VR space and the distance of the user position in the VR space to the particular object in the VR space;
changing the intensity level of the aroma based on the change in the user position in the VR space and change in the distance of the user position in the VR space to the particular object in the VR space;
receiving a response from the user indicating a user selection of an object in the VR space;
revealing the particular object to the user in the VR space and an indication of whether the object selected by the user is the same as the particular object.

16. The non-transitory computer readable medium of claim 15, wherein the operations comprise:
displaying to the user in the VR space the plurality of objects;
receiving a response from the user indicating a selection of an object from the plurality of objects, wherein, in response to the user selection of an object, dispersing the aroma associated to the object;

receiving a response from the user indicating a selection of two objects from the plurality of objects; and in response to selecting two objects from the plurality of objects, displaying to the user whether the two selected objects have the same aroma.

\* \* \* \* \*